(12) United States Patent
Chung et al.

(10) Patent No.: US 6,960,159 B2
(45) Date of Patent: Nov. 1, 2005

(54) SELF-OPERATED MINI THERAPEUTIC DEVICE FOR VENOUS THROMBUS PROPHYLAXIS

(75) Inventors: Shyang-Fong Chung, Kaohsiung (TW); Zequn Sun, Kwangchow (CN)

(73) Assignee: Chia Jei Technology Business Co., Ltd., Kaohsiung (TW)

(*) Notice: Subject to any disclaimer, the term of this patent is extended or adjusted under 35 U.S.C. 154(b) by 0 days.

(21) Appl. No.: 10/825,161

(22) Filed: Apr. 16, 2004

(65) Prior Publication Data
US 2005/0197523 A1    Sep. 8, 2005

(51) Int. Cl.⁷ .............. A61N 1/00; A61H 9/00
(52) U.S. Cl. ....................... 600/15; 601/151
(58) Field of Search ............ 600/9–15; 128/903, 128/904, DIG. 20; 601/148–152, 11–12; 606/201, 202

(56) References Cited

U.S. PATENT DOCUMENTS

| | | | | |
|---|---|---|---|---|
| 4,480,596 A | * | 11/1984 | Shumiyashu | 600/15 |
| 6,213,933 B1 | * | 4/2001 | Lin | 600/13 |
| 6,290,662 B1 | * | 9/2001 | Morris et al. | 601/149 |
| 6,494,852 B1 | * | 12/2002 | Barak et al. | 601/151 |

* cited by examiner

*Primary Examiner*—John P. Lacyk
(74) *Attorney, Agent, or Firm*—Bacon & Thomas, PLLC

(57) ABSTRACT

A self-operated mini therapeutic device for venous thrombus prophylaxis, including plural "Z" shape air passages and plural magnets defined in an air cushion, a mouth of the respective air passages connected to diverting valve via pipes, the diverting valve connected to an inflating and extracting mechanism via the pipes, so as to form air paths for inflation and extraction of the respective air passages in the air cushion, a control circuit employed to control the diverting valve. The self-operated mini therapeutic device can use pressure wave and magnetic stimulation to prevent and treat venous thrombus.

3 Claims, 9 Drawing Sheets

SELF-OPERATED MINI THERAPEUTIC DEVICE FOR VENOUS THROMBUS PROPHYLAXIS

BACKGROUND OF THE INVENTION

1. Field of the Invention

The present invention relates to a therapeutic device, and more particularly to a self-operated mini therapeutic device that can use pressure wave and magnetic stimulation to prevent and treat venous thrombus.

2. Description of the Prior Arts

According to clinical observation, the peoples after operation, anesthesia, long time bedridden or the disabilities, such as the patients suffering from paraplegia, out of conscious, or the healthy peoples after long time of sitting or standing, they are susceptible to so-called deep venous thrombus which happens in the deep vein at the patients' thigh or buttocks. The thigh muscles lack of exercise or the partial blood vessels are injured or the blood viscosity of the lower part of the body is too high, all these factors will engender the venous thrombus. Clinics show that if a blood clot moves from deep vein to lung, which can lead to sudden death by lung clot, or it will interfere the cardiovascular blood circulation that also endangers the life of the patient.

Humen are susceptible to varicose veins of lower limbs because we walk on two legs, which results in valve failure and stagnant blood. The pregnant women are also susceptible to varicose veins of lower limbs due to the increment of the progestational hormone and hypervolemia.

The solution of eliminating or preventing the above-mentioned symptoms is to improve the blood circulation and make it flow smoothly. The blood circulation depends not only on the cardiac contraction but also on the muscle contraction. Since over half of the muscles are located in lower limbs, the legs play the role of a "second heart".

In clinical practices or in particular environments, besides medicines can be used to improve the blood circulation, it is also very important to take some auxiliary measures to prevent, control or treat such kind of deceases.

Conventional method is to apply intermittent compression to patient's legs so as to improve the blood circulation. According to a thesis of "External Pneumatic Intermittent Compression on Fibrinolysis in Man" by Allenby et al published in "The Lancet" of Dec. 22, 1973, which discloses that the Fibrinolysis in patient's body will be inhibited after operation, and the pneumatic intermittent compression in the thighs will encourage the fibrinolysis. The author further discloses that the best way of preventing the after-operation venous thrombus is to apply pneumatic intermittent compression to the patent's shank in or after operation.

Furthermore, from hemorheological point of view, the blood viscosity can be decreased only when subjected to enough shearing stresses, especially the blood in the deep vein of the legs needs more high shearing stresses then the blood circulation can be activated and improved. Since the veins have venous valves, the axial shearing stresses in the veins should be maintained in a higher level then the blood circulation runs smoothly.

However, due to the structural limitation of the air sacs of the conventional portable pneumatic therapeutic device for treatment of venous thrombus, which only uses the vertical compression of the air sacs to the body surface. As disclosed in U.S. Pat. No. 6,290,662 of Sep. 18, 2001, wherein a portable self-operated device for deep venous thrombus prophylaxis only has vertical compression on the patient's body so that the viscose blood in the deep and shallow veins will only reciprocate between two or several venous valves, and the blood circulation cannot be improved. Moreover, since the air sac is too big, it needs long time to inflate the air to a desired pressure.

In addition, many documents have disclosed that magnetic stimulation has positive effect on muscle nerves, e.g. Wen-Hau Lin disclosed in U.S. Pat. No. 6,213,933 of Apr. 10, 2001, that magnetic stimulation could stimulate fibrinolysis. However, so far the magnetic stimulation device of prior arts is not portable, let alone a mini therapeutic device with functions of pneumatic compression and magnetic stimulation.

So far, all the devices with the similar functions, whatever portable or not, they have very limited treatment effect due to the strength and the acting level are inappropriate which cannot satisfy the demands of the physiological pulsation of the deep veins and the peripheral nerves and muscle tissues. The way the devices operate is monotonic and some effects are even unsuitable. And the portability of the so-called "portable" is also limited due to the air sacs should be big enough for maintaining useful effect.

The present invention has arisen to mitigate and/or obviate the afore-described disadvantages of the conventional therapeutic device.

SUMMARY OF THE INVENTION

The primary object of the present invention is to provide a self-operated mini therapeutic device for venous thrombus prophylaxis that not only can produce an effect of waving osmotic pressure that meets the demands of the physiological pulsation, but also can provide flexible and multiple compression effects, besides, it also can provide magnetic stimulation for the target parts of the patient's body.

The self-operated mini therapeutic device for venous thrombus prophylaxis in accordance with one aspect of the present invention comprises plural "Z" shape air passages and plural magnets defined in an air cushion, a mouth of the respective air passages connected to diverting valve via pipes, the diverting valve connected to an inflating and extracting mechanism via the pipes, so as to form air paths for inflation and extraction of the respective air passages in the air cushion, a control circuit employed to control the diverting valve.

The air cushion can be attached to the target parts, such as shank or rear portion of the shank, the foot or sole or the instep of the foot, the buttocks and the arms, etc. A mini air pump can inflate and extract the air passages according to the predetermined program, so as to produce transversal contraction and relief of the deep veins and the neighboring muscles and cause vertical waving movement. Meanwhile, the magnets on the surface of the air passages can move a little along with the movement of the air passages, such that the motion of the magnetic lines will induce the changes of the bioelectricity that located at the adjacent of the deep veins of the muscle tissues.

The self-operated mini therapeutic device for venous thrombus prophylaxis can treat the muscle nerves and the deep vein around the air cushion with waving osmotic pressure and magnetic stimulation, such that the deep venous thrombus can be effectively prevented and the blood circulation is improved. In addition, the structure of the air passages of the present invention can effectively improve the useful works, and the self-operated mini therapeutic device is compact and portable.

The present invention will become more obvious from the following description when taken in connection with the

DETAILED DESCRIPTION OF THE PREFERRED EMBODIMENTS

Figure 1:
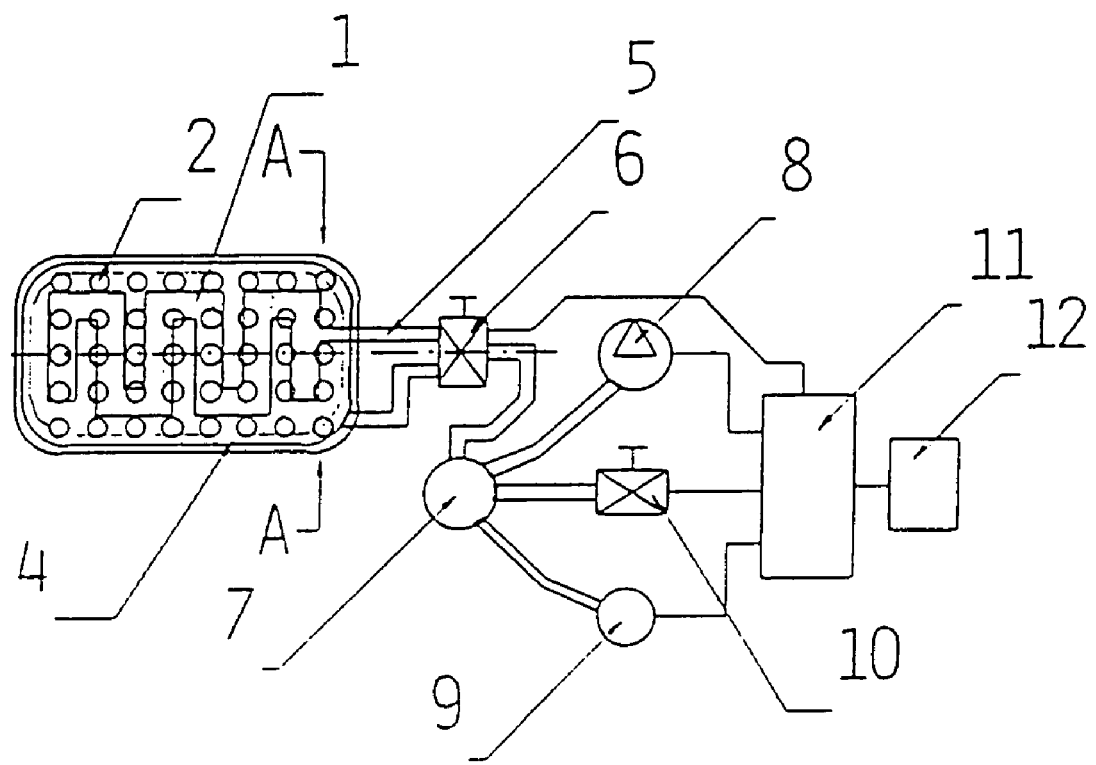
FIG. 1 is an illustrative view of a self-operated mini therapeutic device for venous thrombus prophylaxis in accordance with one aspect of the present invention.
Figure 2:
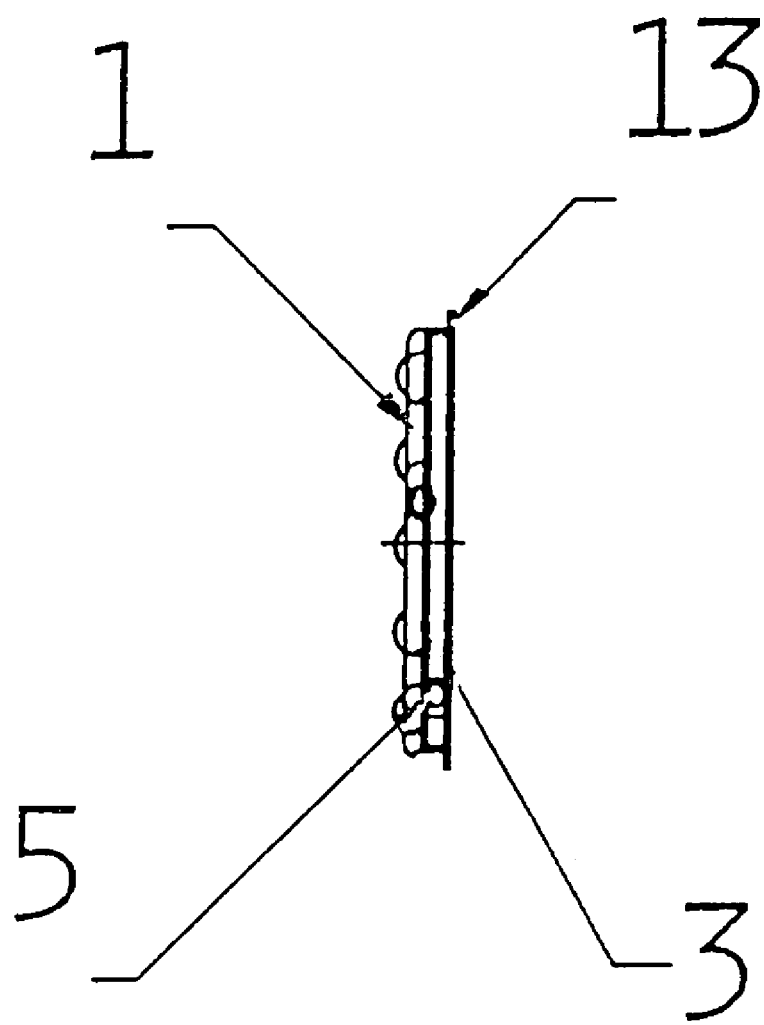
FIG. 2 is a cross sectional view taken along the line A—A of FIG. 1.
Figure 3:
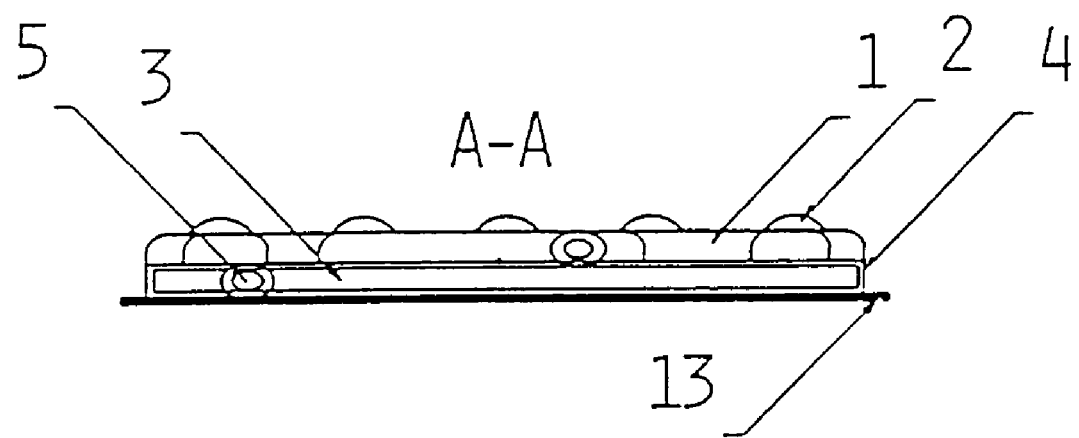
FIG. 3 is amplified view of FIG. 2.

Referring to FIGS. 1–3, wherein a self-operated mini therapeutic device for venous thrombus prophylaxis in accordance with one aspect of the present invention is shown, which comprises: an air cushion 4 has a non-elastic outer layer 13 adhered with a flexible inner liner, the air cushion 4 is interiorly formed with air passage, it can be a single air passage, double air passages or multiple passages, the air passages are parallel with each other, or formed in the shape of "Z". The width of the respective air passages is approximately 50–300 mm, on the surface of the air passages is evenly provided with tiny magnets. The magnetic field strength of each tiny magnet is approximately 2–120 T. The longitudinal and the lateral distances between each adjoining magnets are approximately 10–30 mm. An inflating and extracting mechanism includes a diverting valve 6, a mini air pump 8, a baroceptor 9 and a relief valve 10 which are connected to a multi-way connector 7 via pipes 5. The max input pressure of the inflating and extracting mechanism is approximately 20–300 mmHg. A passage 1 or 3 is connected to the diverting valve 6, with the pipes 5 the diverting valve 6 is connected to the mini air pump 8, the baroceptor 9 and the relief valve 10 via the multi-way connector 7. A control circuit 11 is used to control the mini air pump 8, the baroceptor 9, the relief valve 10 and the diverting valve 6. The control circuit 11 is provided with power source and switch 12.

The air passage arranged in the shape of "Z" is a very special feature of the present invention. Experiments by the inventor have shown that "Z" shape air passage can generate enough shearing stresses to decrease the blood viscosity. The combination of "Z" shape air passages and plural magnets is proved by experiments of the inventor that great effect to decrease the blood viscosity is achieved.

The control circuit 11 includes an oscillator comprised of a set of programming switches and a general purpose integral circuit, a NAND Gate and an output circuit. The control circuit 11 can use program to control the speed of the air inflation/extraction, the sequence of inflation/extraction of the respective air passages, and the working period of the self-operated mini therapeutic device for venous thrombus prophylaxis.

To prolong the service life of battery, a detector for detecting the movements of limbs and trunk (muscular movements) can be used to signal to stop the self-operated mini therapeutic device for venous thrombus prophylaxis whenever the user is walking or doing other activities.

To make it more adaptive to physiological requirements, the self-operated mini therapeutic device for venous thrombus prophylaxis can be additionally equipped with a monitoring equipment which serves to monitor pulses and blood pressure, and the detected data and parameters can be inputted to the control circuit as a basis for the mini therapeutic device to decide the mode of operations.

Figure 4:
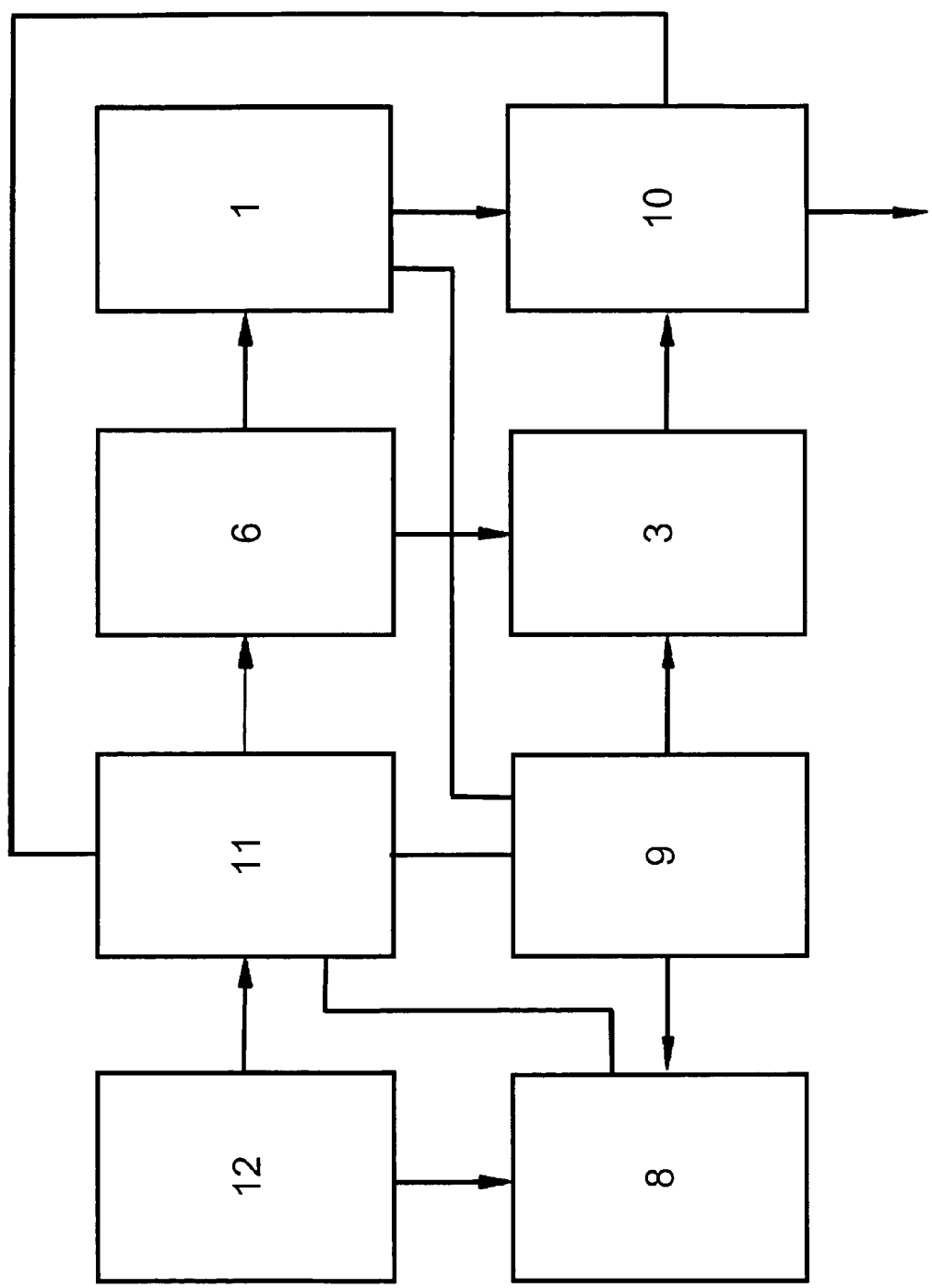
FIG. 4 is an operation block diagram of the self-operated mini therapeutic device for venous thrombus prophylaxis in accordance with one aspect of the present invention.

FIG. 4 is an operation block diagram of the self-operated mini therapeutic device for venous thrombus prophylaxis in accordance with one aspect of the present invention.

Figure 5:
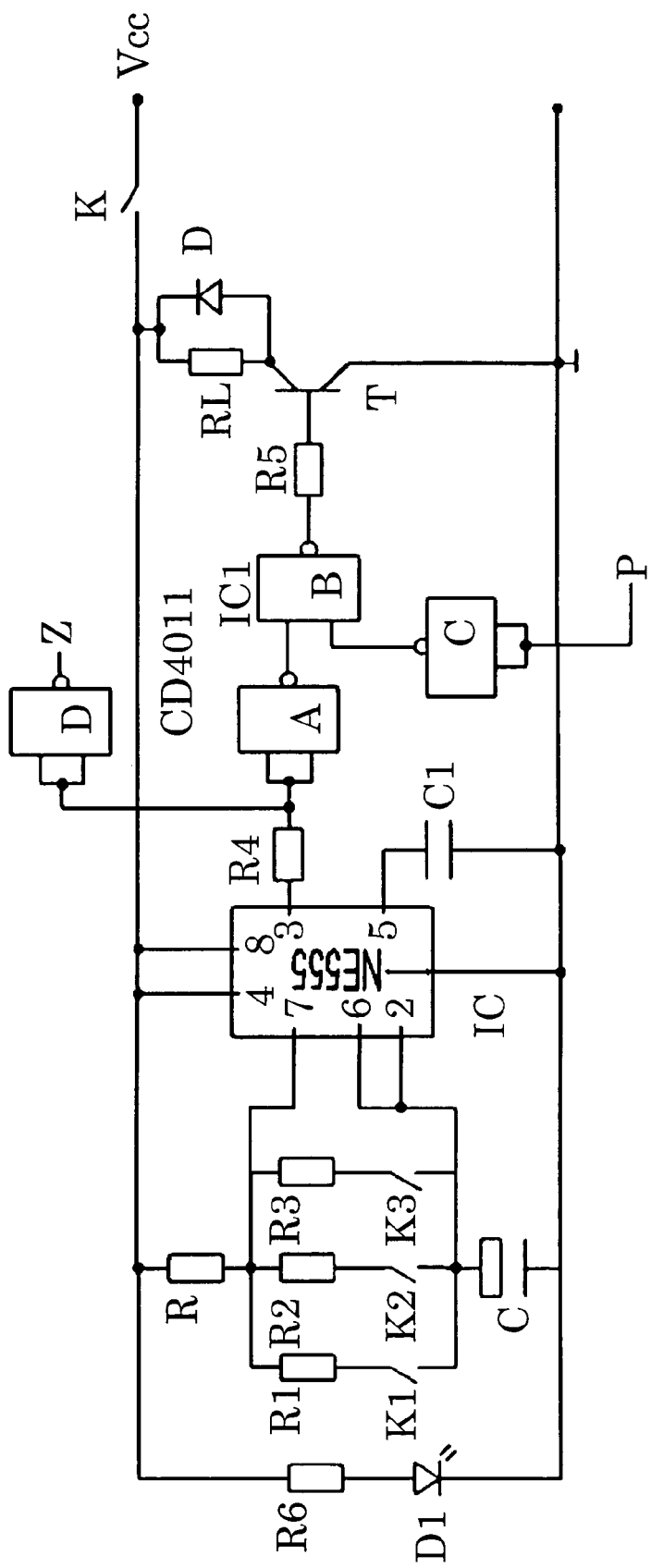
FIG. 5 is a circuit diagram of the self-operated mini therapeutic device for venous thrombus prophylaxis in accordance with one aspect of the present invention.

FIG. 5 is a circuit diagram of the self-operated mini therapeutic device for venous thrombus prophylaxis in accordance with one aspect of the present invention, wherein the control circuit comprises DC power supply of 2.5–6V, oscillating circuit, amplifier circuit, programmer, kinesthetic receptor and switch. A control circuit consisting of a 555 IC, a set of programmable switches (K1, K2, K3, . . . . Ki), NAND Gate and output is used to drive the load RL, the load RL can be mini air pump or relay (with the relay to drive the mini pump). When the switch K is closed, the output end of the IC is at high electric level, and a current-limiting resistor R4 and an inverter 1 are used to trigger the input end of a NAND 2 of the IC1. At this moment, if pressure is not at a predetermined level, position P is at high electric level, thereby the output end T of the control circuit is in fully conducted state, such that the load RL is in operating state. After a period of operation of the load RL, the pressure will reach the predetermined level, the position P is at a low electric level, the output end T of the control circuit is in a cut-off state, and thus the load RL will stop. Power resource Vcc can be dry battery. With this optimized electrical circuit, the work time of the battery can be prolonged up to several weeks.

According to real needs, period of inflation/extraction cycle can be changed from once per minute to once per 10–20 minutes with the change of the resistance of the programmable switches.

In operation, with the mini air pump, the pressure in the air passages can reach a level that is high enough to increase the venous blood return. Through proper adjustment or improvement of the electric circuit, the max pressure can be adjusted. The control circuit of the present invention employs a controllable multi-way diverting valve to realize faster air extraction and flexible multiple-passage air extraction. The air pressure in the air passages can be maintained for a period of time according to needs.

Figure 6:
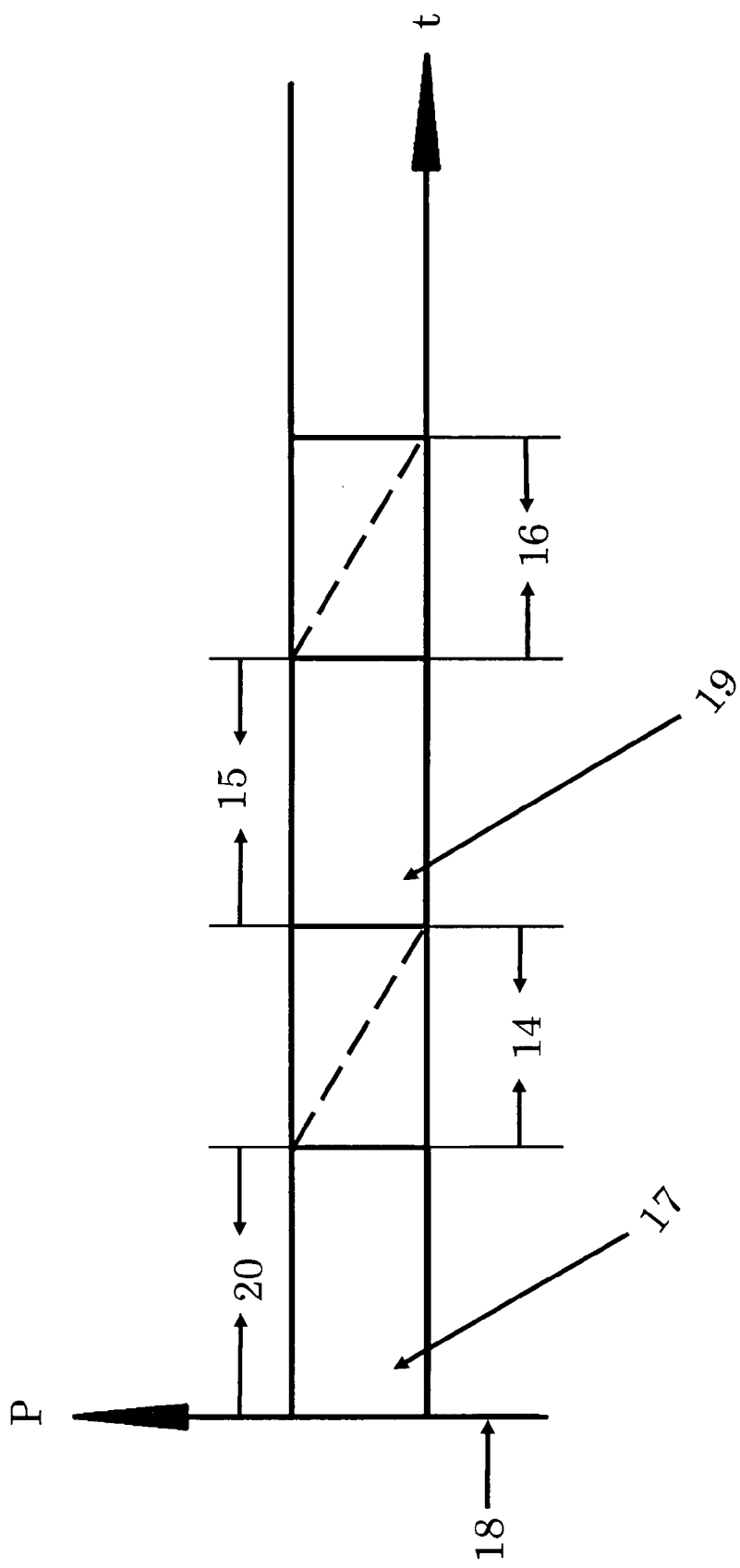
FIG. 6 is an illustrative view for showing the inflation and extraction in the air passages.

The operation of the self-operated mini therapeutic device for venous thrombus prophylaxis in accordance with the present invention is further explained in FIG. 6. The power is turned on at time of 18, and the programmable switches in FIG. 5 are used to adjust the frequency. During the first period 17, the mini air pump 8 inflates the respective air passages for a first time 20 until the baroceptor 9 detects a predetermined max pressure (at the end of the time 20), the circuit starts to count time, that means a first lag phase 14 is started. The diverting valve 6 and the relief valve 10 operate in a coordinate manner during the first lag phase 14, so as to relieve or maintain the air pressure in the respective air passages.

Time count stops at the moment the first lag phase 14 is terminated, then starts a second period 19, the mini air pump 8 operates for a second time 15. In the second period 19, under the control of programmable circuit, the mini air pump 8 starts to choicely inflate the air passages which are selected by the diverting valve 6 until all the air passages in the air cushion 4 to be inflated have been inflated, such that an inflation cycle is finished, and then the next inflation cycle starts until the power is off. The maintenance or relief of the air pressure in the respective air passages can be achieved by the coordination between the relief valve 10 and the diverting valve 6 that is controlled by the programmable circuit. An extreme condition is that with a predetermined program, all the respective air passages in the air cushion are inflated to a predetermined pressure and then the air passages are released in turn, that is to say, with a more complicated programmable circuit or microprocessor, the inflation speed, the time delay of pressure-release or the periodical change between the air inflation and release can be adjusted synchronously or respectively according to their corresponding time functions. Therefore the self-operated mini therapeutic device for venous thrombus prophylaxis in accordance with the present invention is not only conductive to specific treatment but also helpful to the service life of the battery.

Figure 7:
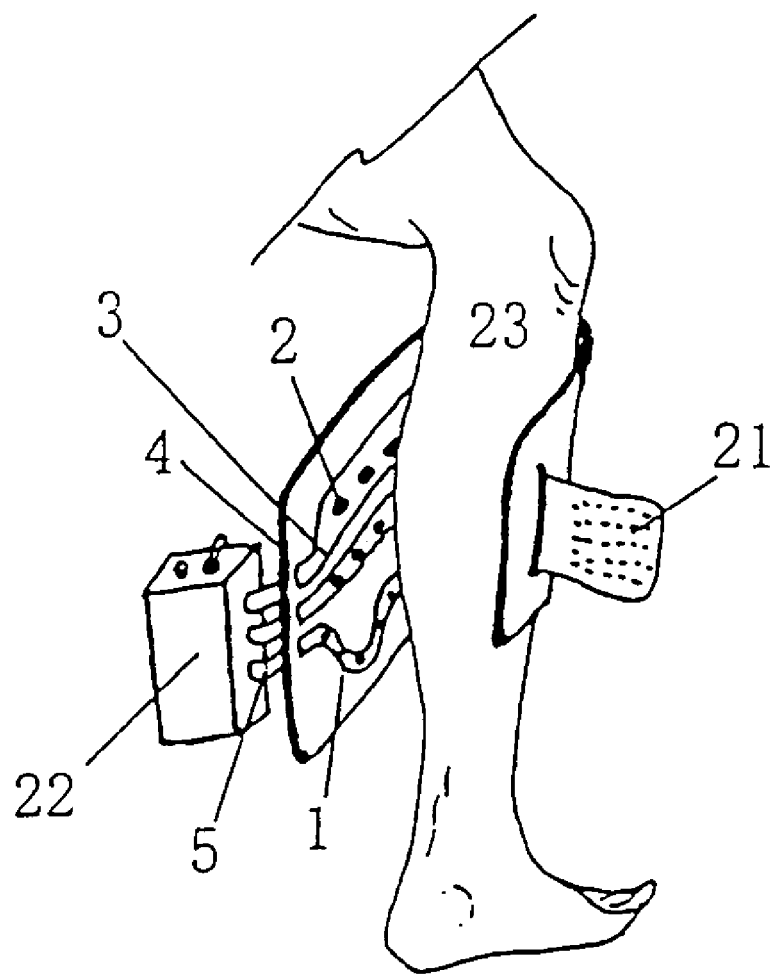
FIG. 7 is a stereographic view for showing the self-operated mini therapeutic device for venous thrombus prophylaxis attached to user's shank.

As shown in FIG. 7, wherein the air cushion 4 is attached to a user's shank 23 and fixed with a nylon buckle 21, the air passages 1 or 3 are connected to a control box 22 for air path and circuit. The diverting valve 6, the inflating and extracting mechanism and the circuit for controlling them are enclosed in the control box 22. A rotary knob is defined on the control box 22, when the power is turned on, the mini air pump 8 in the control box 22 will inflate or extract the respective air passages, so as to massage the shrank with wave pressure, meanwhile a magnet 2 in the air cushion also will have effect on the shrank.

Figure 8:
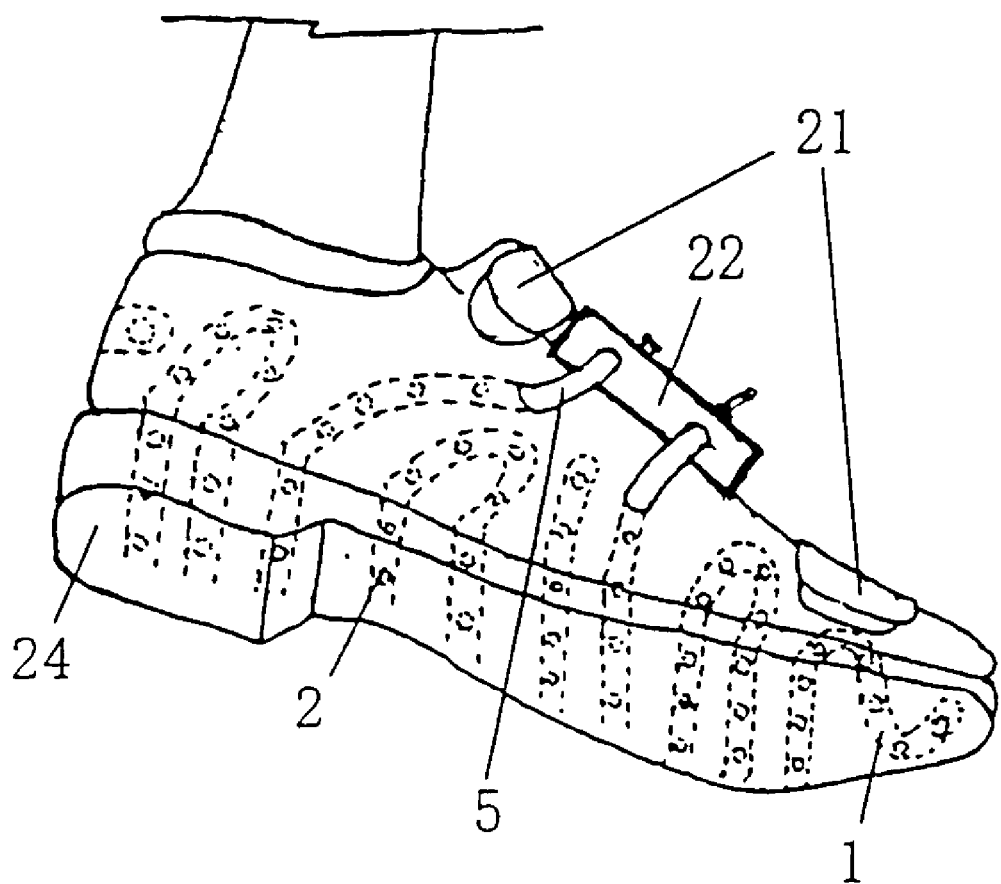
FIG. 8 is a perspective view for showing the self-operated mini therapeutic device for venous thrombus prophylaxis attached to user's foot.

Referring to FIG. 8, wherein the air cushion in accordance with another embodiment of the present invention is disposed in the user's shoe 24 at a position corresponding to the sole and the side of the foot. The mini air pump 8 and the control box 22 can be positioned on the front uppers of the shoe and connected to the air passages 1 via the pipe 5.

Figure 9:
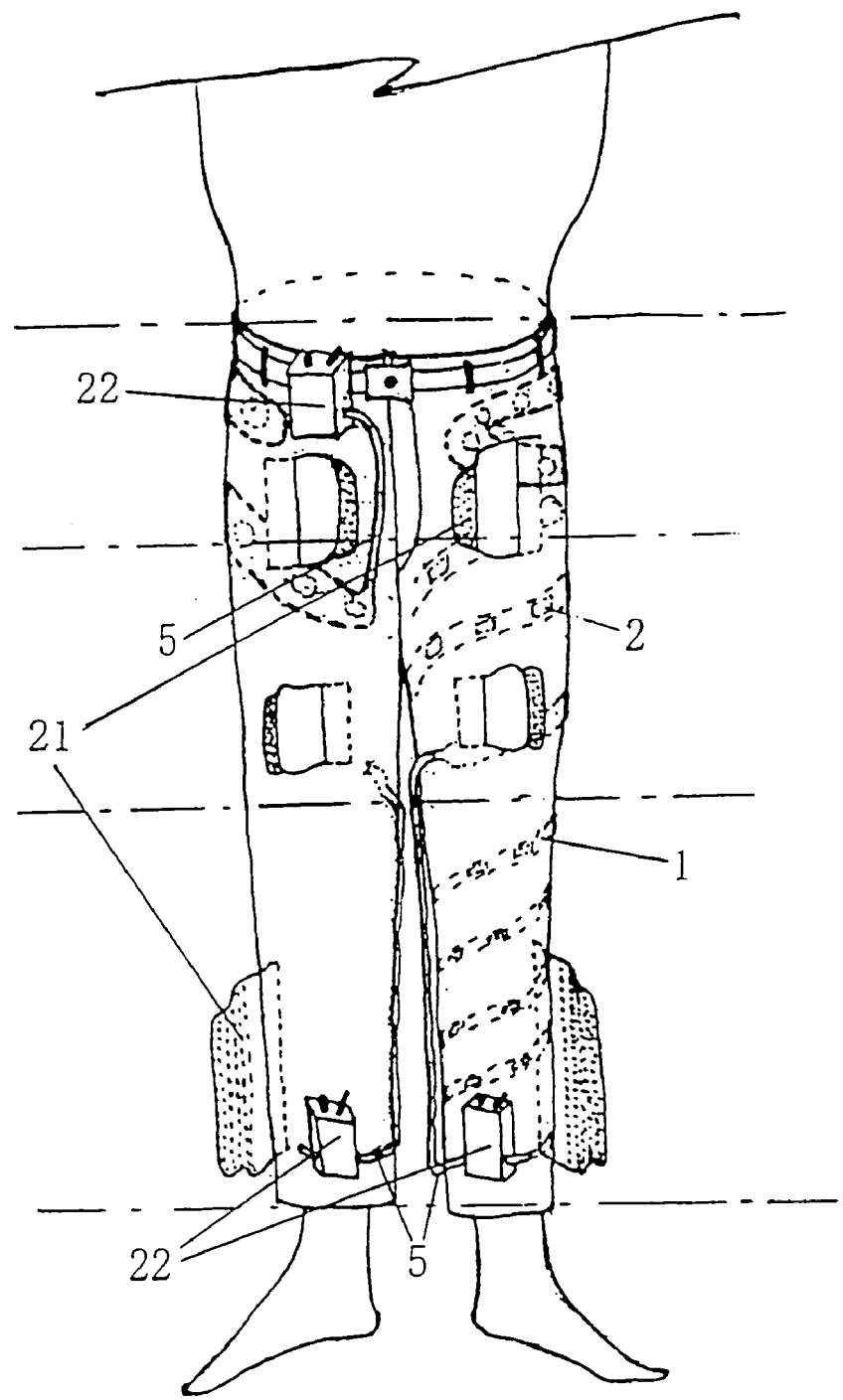
FIG. 9 is a perspective view for showing the self-operated mini therapeutic device for venous thrombus prophylaxis attached to user's pants.

Referring to FIG. 9, wherein the air cushion with multiple air passages in accordance with another embodiment of the present invention is fixed to pants. In this embodiment, the air passages 1 are respectively located at the positions of the buttock, the thigh and the shank. In consideration of limitation of the position and the power capacity, wherein the air cushion at the positions of the buttock, the left thigh and shank, and the right thigh and shank are connected to three air paths via three pipes 5 and controlled by the control box 22. Obviously, if pneumatic component parameter can meet the desired power requirements, they can be combined together, the arrangements of the air paths and the magnets include but are not limited to the positions as shown in Figures. In real operation, the user only needs to fasten the nylon buckle 21 to desired parts of the body and turn the power on, and then the self-operated mini therapeutic device for venous thrombus prophylaxis works immediately.

While we have shown and described various embodiments in accordance with the present invention, it should be clear to those skilled in the art that further embodiments may be made without departing from the scope of the present invention.

What is claimed is:

1. A self-operated mini therapeutic device for venous thrombus prophylaxis, comprising plural air passages and plural magnets defined in an air cushion, a mouth of each of the air passages connected respectively to a diverting valve via pipes, the diverting valve connected to an inflating and extracting mechanism via the pipes, so as to form air paths for inflation and extraction of the respective air passages in the air cushion, a control circuit employed to control the diverting valve and the inflating and extracting mechanism;

wherein the air cushion has a non-elastic outer layer adhered with a flexible inner liner, the air cushion is interiorly formed with the air passages which are arranged in the shape of "Z", the width of the respective air passages is 50–300 mm, tiny magnets are evenly provided on a surface of the air passages, a magnetic field strength of the respective tiny magnets is 2–120 T, a longitudinal distance and a lateral distance between each adjoining magnets are 10–30 mm;

wherein the inflating and extracting mechanism has the diverting valve, a mini air pump, a baroceptor and a relief valve which are connected to a multi-way connector via the pipes, a max input pressure of the inflating and extracting mechanism is 20–300 mmHg.

2. The self-operated mini therapeutic device for venous thrombus prophylaxis as claimed in claim 1, wherein the control circuit comprises a DC power source of 2.5–6V, an oscillating circuit an amplifier circuit, a programmer, a kinesthetic receptor and a switch.

3. The self-operated mini therapeutic device for venous thrombus prophylaxis as claimed in claim 1, wherein the diverting valve, the inflating and extracting mechanism, and the control circuit employed to control the diverting valve and the inflating and extracting mechanism are enclosed in a control box.

\* \* \* \* \*